United States Patent
Montes et al.

(10) Patent No.: US 9,352,012 B2
(45) Date of Patent: May 31, 2016

(54) PROCESS FOR THE PREPARATION OF PHARMACEUTICAL COMPOSITIONS FOR THE SUSTAINED RELEASE OF SOMATOSTATIN ANALOGS

(75) Inventors: Martin Montes, Sant Quirze del Vallés (ES); Thomas Ciaran Loughman, Killester (IE); Chantal Roume, Signes (FR); Roland Cherif-Cheikh, Castelldefels (ES)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 500 days.

(21) Appl. No.: 13/522,297

(22) PCT Filed: Jan. 11, 2011

(86) PCT No.: PCT/EP2011/000069
§ 371 (c)(1),
(2), (4) Date: Dec. 7, 2012

(87) PCT Pub. No.: WO2011/085957
PCT Pub. Date: Jul. 21, 2011

(65) Prior Publication Data
US 2013/0079282 A1    Mar. 28, 2013

Related U.S. Application Data (60) Provisional application No. 61/294,644, filed on Jan. 13, 2010.

(51) Int. Cl.
| A61K 38/31 | (2006.01) |
| A61K 38/12 | (2006.01) |
| C07K 7/50  | (2006.01) |
| A61K 9/19  | (2006.01) |
| A61K 9/00  | (2006.01) |
| A61K 47/12 | (2006.01) |

(52) U.S. Cl.
CPC .............. *A61K 38/12* (2013.01); *A61K 9/0019* (2013.01); *A61K 9/19* (2013.01); *A61K 38/31* (2013.01); *A61K 47/12* (2013.01)

(58) Field of Classification Search
None
See application file for complete search history.

(56) References Cited

U.S. PATENT DOCUMENTS

| 6,503,534 B1 * | 1/2003 | Pellet et al. ............... 424/464 |
| 2007/0116729 A1 * | 5/2007 | Palepu ..................... 424/400 |
| 2011/0178013 A1 | 7/2011 | Paternostre et al. |

FOREIGN PATENT DOCUMENTS

| CN | 1415378    | * | 5/2003 |
| EP | 1595532    |   | 11/2005 |
| FR | 2762319    |   | 10/1998 |
| WO | 2009040035 |   | 4/2009 |

OTHER PUBLICATIONS

International Search Report for PCT/EP2011/000069 mailed Mar. 12, 2012.
Somatuline Depot (lanreotide acetate); Approved Aug. 2007.

* cited by examiner

*Primary Examiner* — Satyanarayana R Gudibande
(74) *Attorney, Agent, or Firm* — Hunton & Williams LLP (57) ABSTRACT

The invention relates to a process for the preparation of injectable pharmaceutical compositions for the sustained release of somatostatin analogues and to pharmaceutical compositions prepared according to the process. In a preferred aspect the process comprises the steps of combining lanreotide acetate and acetic acid, lyophilizing the resulting mixture only once, and hydrating the lyophilizate. Acetic acid may be added to a desired pH during the final step of the process.

22 Claims, 3 Drawing Sheets

PROCESS FOR THE PREPARATION OF PHARMACEUTICAL COMPOSITIONS FOR THE SUSTAINED RELEASE OF SOMATOSTATIN ANALOGS

This application is a national stage filing of PCT/EP2011/000069, filed Jan. 11, 2011, the subject matter of which is incorporated herein in its entirety. This application further claims priority to U.S. Provisional Patent Application No. 61/294,644, filed Jan. 13, 2010, the subject matter of which is incorporated herein in its entirety.

The invention relates to a process for the preparation of pharmaceutical compositions for the sustained release of somatostatin analogues and to pharmaceutical compositions prepared according to said process.

The invention further relates to pharmaceutical compositions for the sustained release of the somatostatin analogue lanreotide.

Many peptide treatments require continuous or repeated administration in the patient over an extended period of time. As repeated injections cause both inconvenience and discomfort to the patient, sustained release preparations are desirable and have been the subject of development efforts.

Various processes are known for the preparation of sustained release of peptides. However, the processes are often relatively complex and may not consistently produce the same product.

International Patent Publication WO 2004/030650 discloses a preparation for the sustained release of a GnRH antagonist. In contrast to the present application is gozarelix [INN name], an antagonist of releasing factor luteinizing hormone (LHRH), used in patients suffering from benign prostatic hyperplasia (BPH) previously known by its development code D-63153. The publication discloses reconstituting a lyophilized peptide with a low-concentration inorganic salt solution to a concentration of from 5 mg to 50 mg of peptide per milliliter. Administration of the resulting preparation is contemplated up to two hours after the reconstitution.

U.S. Pat. No. 5,595,760 describes solid and semi-solid pharmaceutical compositions intended for the sustained release of peptides, which compositions are composed of a gellable and water-soluble peptide salt optionally combined with an appropriate monomeric excipient. These compositions gel after administration to a patient and allow a sustained release over a period of at least three days.

International Patent Publication WO 99/48517 discloses a solid or semi-solid pharmaceutical composition comprising a gellable and water-soluble peptide salt. The process for the preparation of the composition involves two lyophilization steps and the addition of an acid to regulate the final pH is not disclosed.

The applicant has now discovered that a simpler process involving a single lyophilization step may be employed to produce compositions according to the invention.

It is an object of the invention to provide a simpler process for the preparation of injectable compositions for the sustained release of somatostatin analogues. It is a further object of the invention to produce compositions consistently having a pH within a relatively narrow range.

A subject of the present invention is therefore a process for the preparation of an injectable sustained release pharmaceutical composition, comprising the steps of:

combining a gellable somatostatin analogue salt and an aqueous acid solution;

lyophilizing the resulting mixture only once; and hydrating the lyophilizate;

wherein the final pH of the composition ranges between pH 5 to 7.

Unless otherwise indicated, the following definitions are set forth to illustrate and define the meaning and scope of the various terms used to describe the invention herein.

The term "pharmaceutically acceptable" means in this context physiologically well-tolerated by a mammal or a human.

The term "gellable" means the capability of a compound to form semi-solid products, with viscosity suitable for parenteral administration, when mixed with pure water, aqueous solutions containing and acid or basic agent suitable to adjust the pH or other solvents suitable for parenteral administration in humans.

Somatostatin analogue is understood as meaning a somatostatin derivative or analogue such as lanreotide as described in the European Patent EP 215171, or a somatostatin analogue such as that described in the U.S. Pat. No. 5,552,520 (this patent itself includes a list of other patents describing somatostatin analogues, which are incorporated in the present application by way of reference).

The somatostatin analogue used for the invention may be selected from the group comprising lanreotide [BIM 23014], octreotide and BIM-23244, a somatostatin receptor subtype 2- and 5-selective analogue.

The salts of the somatostatin analogue which can be used for the invention are preferably pharmaceutically acceptable salts of organic acids, such as those of acetic, lactic, malic, ascorbic, succinic, benzoic, methanesulphonic or toluenesulphonic acids, or pharmaceutically acceptable salts of inorganic acids, such as those of hydrochloric, hydrobromic, hydriodic, sulphuric or phosphoric acids. In particular, they can be acetates of the somatostatin analogue.

The somatostatin analogue lanreotide, also known by the development code BIM 23014, is sold in the form of lanreotide acetate under the trade mark SOMATULINE®. Lanreotide acetate is a synthetic cyclic octapeptide analog of the natural hormone somatostatin. Lanreotide acetate is chemically known as [cycloS—S]-3-(2-naphthyl)-D-alanyl-L-cysteinyl-L-tyrosyl-D-tryptophyl-L-lysyl-L-valyl-Lcysteinyl-L-threoninamide, acetate salt. Its molecular weight is 1096.34 (base) and its developed formula is:

The somatostatin analogue BIM 23244 is the compound DPhe-c(Cys-3I Tyr-DTrp-Lys-Val-Cys)-Thr-NH$_2$ ($C_{50}H_{66}IN_{11}O_{10}S_2$).

In a preferred embodiment, the somatostatin analogue used for the invention is selected from the group comprising lanreotide [BIM 23014] and octreotide.

In a preferred embodiment, the somatostatin analogue is lanreotide. In a preferred embodiment, the somatostatin analogue is octreotide.

In a preferred embodiment, the acid is acetic acid.

In a preferred embodiment, the somatostatin analogue is lanreotide and the acid is acetic acid.

The acetic acid used in a preferred embodiment of the invention may be in the form of glacial acetic acid, and may have a purity of 95% to 99.7% or higher, preferably have a purity of 95%, 98%, 99%, 99.7% or higher, and more preferably 99.7% or higher.

In a preferred embodiment, the final step in the inventive process enables the addition of acid, as necessary, to produce compositions of relatively consistent pH. Hence the water used to hydrate the lyophilizate preferably contains acid at a concentration suitable for providing the requisite final pH. More preferably water used to hydrate the lyophilizate preferably contains acetic acid at a concentration suitable for providing the requisite final pH, and/or to render the anhydrous acetate content of the pharmaceutical composition of 9±2% by weight. More preferably water used to hydrate the lyophilizate preferably contains acetic acid at a concentration suitable for providing the requisite final pH, and/or to render the anhydrous acetate content of the pharmaceutical composition 9.7±0.3% by weight.

This aspect of the invention has the advantage of facilitating better control over the pH, providing compositions of more consistent final pH. Reducing experimental deviations in the final pH is important. As the pH governs a number of key parameters including the solubility of the API (active pharmaceutical ingredient) in the pharmaceutical composition. Therefore, the viscosity of the formulation also depends on the pH and consequently, the force required to inject the composition and solubility of the drug substance within the pharmaceutical composition. Reducing the force required to inject the composition facilitates the use of syringe needles of smaller diameter which improves convenience of use. The solubility of the drug substance governs the formation of the depot at the injection site. Once formed the API (active pharmaceutical ingredient) is slowly released from the depot by dissolution and passive diffusion to the surrounding tissue.

In a further preferred embodiment, in the lyophilization step, the temperature of the mixture during the lyophilization is preferably:

initially reduced from room temperature to 2° C.±1° C. and then retained constant;
further reduced from 2±1° C. to −40±5° C. and then retained constant;
initially increased from −40±5° C. to 25±5° C. and then retained constant; and
further increased to 35±5° C. and then retained constant.

In a further preferred embodiment, the temperature of the mixture during the lyophilization step is successively:

step a: initially reduced from room temperature to 2° C.±1° C. and then retained constant;
step b: further reduced from 2±1° C. to −40±5° C. and then retained constant;
step c: initially increased from −40±5° C. to 25±5° C. and then retained constant; and
step d: further increased to 35±5° C. (step d) and then retained constant.

With regard to the pressure during lyophilization, after the temperature of the mixture is reduced, the atmospheric pressure is preferably reduced to 20±5 µbar and the atmospheric pressure preferably remains constant as the temperature of the mixture increases.

With regard to timing, the duration of the lyophilization process is preferably at least 60 hours. More specifically, during the lyophilization step, the temperature of the mixture is preferably:

initially reduced over up to 30 minutes, preferably up to 10 minutes, and then retained constant for 3±1 hours;
further reduced over up to 15 minutes, preferably up to 10 minutes, and then retained constant for 3.5±1 hours;
initially increased over 20±5 hours and then retained constant for at least 40 hours; and
further increased over 1±0.5 hours and then retained constant for at least 16 hours.

More specifically, during the lyophilization step, the temperature of the mixture is preferably:

during step a: initially reduced over up to 30 minutes, preferably up to 10 minutes, and then retained constant for 3±1 hours;
during step b: further reduced over up to 15 minutes, preferably up to 10 minutes, and then retained constant for 3.5±1 hours;
during step c: initially increased over 20±5 hours and then retained constant for at least 40 hours; and
during step d: further increased over 1±0.5 hours and then retained constant for at least 16 hours.

In another preferred embodiment, 25±2 g/l lanreotide base and 15±2% by weight acetic acid are combined in the first step.

In yet another preferred embodiment, the composition comprises water in an amount less than 50% of the amount needed to completely dissolve the lanreotide salt and the proportion of water is adapted to give the composition a semi-solid consistency. Preferably, where possible, the amount of water added will be less than 30% and more preferably less than 10% of the amount needed to dissolve the somatostatin analogue salt completely.

In a preferred embodiment the final pH of the composition will range from pH 5 to 7. More preferably it will range from pH 5.5 to 6.5. More preferably it will range from pH 5.8 to 6.4. More preferably it will range from pH 5.9 to 6.1

Another subject of the present invention is a pharmaceutical composition prepared according to the process described above.

The composition preferably has an anhydrous acetate content of 7.5±2.5% by weight. Preferably, the composition has an anhydrous acetate content of 9±2% and more preferably, the composition has an anhydrous acetate content of 9.7±0.3% by weight. More preferably, the composition has an anhydrous acetate content of 9.1 to 10.5% by weight.

In a preferred embodiment, the composition is capable of releasing the lanreotide over a period of at least 15 days. Preferably, the composition is capable of releasing the lanreotide over a period of at least 28 days. In a preferred embodiment, the composition is capable of releasing the lanreotide over a period of at least 1 month, and more preferably approximately 2 months (56 days), and more preferably 2 months.

In another preferred embodiment, the composition comprises between 15 to 35%, by weight of lanreotide base. In another preferred embodiment, the composition comprises between 20 and 35% by weight lanreotide base. Preferably, the composition comprises 25±5% by weight lanreotide base. More preferably the composition comprises 24.6±2.5% by weight of lanreotide base. More preferably, the composition comprises approximately 24.6% by weight of lanreotide base.

The composition is preferably suitable for use after storage at between 2 and 8° C. for more than 12 months, preferably for more than 24 months. The composition is preferably suitable for use after storage at 25° C. for 6 months.

As described above, the invention relates in one aspect to a process for the preparation of an injectable sustained release pharmaceutical composition comprising a gellable somatostatin analogue salt and an aqueous acid. The process used to prepare the pharmaceutical compositions of the invention involves a single lyophilization.

It has been found that the pH of the composition effects both its injectability and its release rate. Injectability can be measured either in terms of viscosity (with a higher viscosity resulting in a decrease in injectability), or in terms of flow rate (with a higher flow rate resulting in an increase in injectability). Release rate can be measured by conducting in vitro release tests to determine the percentage of the somatostatin analogue released over time.

Studying the viscosity, flow rate and release rate of a composition containing a given somatostatin analogue enables an acceptable pH range for that somatostatin analogue to be determined.

As previously mentioned, in one embodiment, the somatostatin analogue is lanreotide and the aqueous acid is aqueous acetic acid. In this embodiment, the pH of the composition has been found to be directly proportional to the concentration of acetic acid. It follows that the optimum acetic acid concentration can be calculated from the optimum pH.

A preferred process of the invention involves combining the lanreotide base and the acetic acid, lyophilizing the resulting mixture once, and hydrating the lyophilizate. Detailed conditions under which the process can be performed are set out below; however, the conditions may be varied, for example, when different somatostatin analogues are employed.

The lanreotide base and acetic acid may be combined in a pre-lyophilisation pool which is then loaded into trays. In a preferred aspect the trays are 1.5 or 2 mm thick and the depth of the solution in the trays is 1.2 mm thick or less. The depth of the solution in the trays must be controlled as it has an influence on the final acetate concentration of the pharmaceutical composition.

Prior to the lyophilization, the concentration of lanreotide base is preferably between 20 and 30 g/l, more preferably between 23 and 27 g/l and most preferably 25 g/l, and the concentration of acetic acid is preferably less than 20%, more preferably between 13 and 17% and most preferably 15%.

The lyophilization may be carried out under conventional conditions known to a person skilled in the art.

In a preferred embodiment, the lyophilization process may commence with cooling the solution in the trays to a temperature between room temperature and the temperature at which the solution freezes, preferably between 1 and 5° C. or more preferably 2° C. The temperature may then remain constant for at least one hour, preferably between 2 and 4 hours or most preferably 3 hours. This preliminary cooling step enables the subsequent freezing step to occur more quickly which, in turn, ensures that the frozen ice lattice is more homogeneous.

The lyophiliser shelves may then be further cooled, preferably to less than −20° C., more preferably to less than −30° C., and most preferably to −40±5° C. This cooling step should be completed as quickly as possible, preferably over up to 15 minutes and more preferably over up to 10 minutes or less. The resulting solid is preferably retained at a constant temperature for at least 2 hours, preferably between 2.5 and 4.5 hours, and most preferably for 3.5 hours. The mixture must be cooled for sufficient time so that the entire mixture is frozen prior to sublimation.

The sublimation process may commence with the application of a vacuum, preferably between to 15 to 25 μbar, or more preferably to 20 μbar. The temperature of the shelves may then be initially increased, preferably over at least 10 hours, more preferably between 15 and 25 hours and most preferably 20 hours, preferably to between 20 and 30° C., more preferably to 25° C. The temperature of the solution may then be kept constant, preferably for at least 20 hours, more preferably for at least 40 hours. This primary drying stage removes unbound moisture and acetic acid.

The temperature of the mixture may then be further increased, preferably over at least 15 minutes, more preferably between 0.5 and 1.5 hour, most preferably 1 hour, to a temperature preferably between 30 and 40° C., more preferably 35° C. To complete the lyophilization stage, the temperature of the mixture can be retained constant, preferably for at least 10 hours, more preferably at least 16 hours. This secondary drying stage removes adsorbed moisture and acetic acid.

The lyophilizate resulting from this preferred process is lanreotide acetate having an anhydrous acetate content of less than 10% in weight and preferably less than 9.6%.

The final stage of the process involves hydrating the lyophilizate with water, preferably water for injection.

An equipment consisting of two syringes (cylinders) connected via a three-way valve may be employed to mix the optionally acidified water for injection and the lanreotide acetate. With regard to the device, a person skilled in the art may also usefully consult International Patent Publication WO 96/07398. If such equipment is employed, a vacuum is applied via the three-way valve to the syringe (cylinder) containing the lanreotide acetate powder lyophilizate to reduce the air content within the powder. The water in the second cylinder may then be introduced into the syringe (cylinder) containing the lanreotide acetate, via the three-way valve. The lanreotide acetate may then undergo static hydration, preferably for at least two hours. In order to homogenize the resulting dispersion, the content of the syringe (cylinder) is passed via the valve to the other syringe (cylinder), and this process may be repeated with the reciprocating movement of the two pistons assisted by an electric mixer. The force used to depress each piston may be increased during the mixing process, as the solution becomes more saturated.

As previously mentioned, if the pH of the lyophilizate is above the targeted pH, acid may be added to water for injection prior to the hydration, in an amount suitable for providing the requisite pH in the pharmaceutical composition. The acid used for this purpose is preferably acetic acid.

An important aspect of the invention is the selection of the most appropriate target pH for the composition. Experiments have shown that pH is directly linked to acetic acid concentration, and that these related factors influence both the injectability and the solubility of the drug substance in the pharmaceutical composition With regard to the injectability, an increase in the pH leads to a decrease in the flow rate and an increase in the syringe injection force (SIF), both of which result in decreased injectability. With regard to the release rate, lanreotide acetate concentration (and consequentially pH) influences the solubility of the drug substance within the composition. The solubility of the drug substance governs the formation of the depot at the injection site. An increase in the pH leads to a faster formation of the depot and consequently to a better control of the burst effect in the PK profile. Furthermore, the effect of pH on the solubility of the active substance impacts on the in vitro release test developed for the routine quality control of the drug product. An increase in the pH leads to a decrease in the release profile of the composition.

It follows that in order to produce a composition which is easy to inject and which releases the active ingredient over an extended period of time, a pH must be selected which provides an appropriate compromise between the competing factors injectability and release rate.

In the embodiment where the somatostatin analogue is lanreotide and the acid is acetic acid, experiments have determined that the most appropriate pH range is 5.8 to 6.4, which corresponds to an anhydrous acetate content of the pharmaceutical composition of 9.1 to 10.5% by weight. The water may be conveniently acidified in the manner described above if the concentration of acetate in the solid lyophilizate is such that the pH of the pharmaceutical composition would otherwise be above the acceptable pH range. Adding acetic acid to the water enables the anhydrous acetate content to be increased to the targeted concentration.

The proportion of somatostatin analogue in the compositions according to the invention will be determined by the release time which it is desired to achieve, but it cannot exceed a maximum value corresponding to the limiting concentration at which the solid or semi-solid composition can be injected with a syringe fitted with a needle of customary diameter.

Preferably the compositions of the invention comprise from 18.3 to 42.7% by weight of lanreotide acetate. Preferably the compositions of the invention based on lanreotide acetate will comprise from 25 to 35%, preferably from 25 to 30%, corresponding to 20.5 to 24.6% by weight of pure lanreotide. In a preferred embodiment, the compositions of the invention will comprise 30±3% by weight of lanreotide acetate, corresponding to 24.6±2.5% by weight of lanreotide base.

A range of 25 to 35% by weight of lanreotide acetate in the composition corresponds to a range of 20.5 to 28.7% by weight of pure lanreotide base in the composition. A range of 24.4 to 42.7% by weight of lanreotide acetate in the composition corresponds to a range of 20 to 35% by weight of pure lanreotide base in the composition. A range of 24.4 to 36.6% by weight of lanreotide acetate in the composition corresponds to a range of 20 to 30% by weight of pure lanreotide base in the composition.

The semi-solid compositions according to the invention are for use in the pharmaceutical field. The compositions according to the invention may be administered to a patient, for example, by way of injection using a device such as those described in U.S. Pat. No. 6,953,447. Compositions according to the invention may easily be injected with needles of gauge approximately 17 or 18, which corresponds to an internal diameter of about 1 mm.

Unless defined otherwise, all the technical and scientific terms used here have the same meanings as those commonly understood by an ordinary specialist in the field to which this invention belongs. All the publications, patent applications, patents and other references mentioned here are incorporated by way of reference.

The following examples are given in order to illustrate the above procedures and must not be considered as limiting the scope of the invention.

EXPERIMENTAL PART

The general steps employed in the examples are set out below. Not all of the steps were employed in all of the examples. The general steps are followed by detailed information on each of the examples.

Combining Lanreotide Acetate and Aqueous Acetic Acid, Followed by First Lyophilisation A pre-lyophilization pool was prepared by adjusting the concentration of pure Lanreotide [BIM 23014] to 25±2 g/l in an aqueous solution of 15% acetic acid solution. The pool was loaded into a metal tray and placed in a lyophiliser whose shelves were cooled from room temperature to 2° C. over 10 minutes and then held at this temperature for 3 hours. The cooled mixture was then frozen to −40° C. over 10 minutes and then held at this temperature for 2.75 hours.

To effect the lyophilisation, a vacuum to 20 μbar was applied and maintained while the lyophiliser shelves were heated from −40° C. to 25° C. over 20 hours, held at this temperature for a further 63.3 hours and further heated to 35° C. for 23 hours.

Optional Acidification

Water for injection was acidified with glacial acetic acid.

Hydration of the Lyophilizate

The lanreotide acetate lyophilizate powder was combined with acidified water for injection to a specified concentration of pure lanreotide using the following steps. The lanreotide acetate and water were weighed and placed into two separate cylinders, fitted with pistons and linked together via a three-way valve. Prior to hydration, a vacuum of between 100 and 600 μbar was applied to the cylinder containing the lanreotide acetate powder via the three-way valve. The water was then introduced into the cylinder containing the lanreotide acetate, again via the three-way valve. The lanreotide acetate then underwent static hydration for at least two hours. The dispersion was then homogenised by passing the contents back and forth between the two cylinders via the three-way-valve, using the pistons. The process yielded a lanreotide acetate supersaturated gel.

SUMMARY OF EXAMPLES 1 TO 9

A summary of the specific conditions of each example appears in Table 1, below.

TABLE 1

| Example | | AcOH (% w/w) | | | Lanreotide | |
|---|---|---|---|---|---|---|
| No. | Batch | API | Added | Total | (% w/w) | pH |
| 1 | 04K TS 2202 | 9.9 | 0.0 | 9.9 | 24.83 | 6.01 |
| 2 | DS 361/022 | 9.5 | 0.0 | 9.5 | 24.82 | 6.25 |
| 3 | 04K TS 2205 | 9.2 | 0.0 | 9.2 | 24.75 | 6.41 |
| 4 | 04K TS 2204 | 8.2 | 0.0 | 8.2 | 24.70 | 6.86 |
| 5 | 04K TS 2204 | 8.2 | 0.5 | 8.7 | 24.73 | 6.61 |
| 6 | 04K TS 2204 | 8.2 | 2.5 | 10.7 | 24.60 | 5.78 |

TABLE 1-continued

| Example | | AcOH (% w/w) | | | Lanreotide | |
|---|---|---|---|---|---|---|
| No. | Batch | API | Added | Total | (% w/w) | pH |
| 7 | FFD 04K TS 2205 | 7.5 | 1.2 | 8.7 | 24.88 | 6.51 |
| 8 | N006.21 00006 | 9.7 | 1.3 | 11.0 | 24.88 | 5.73 |
| 9 | FFD 04K TS 2205 | 7.5 | 0.0 | 7.5 | 24.87 | 6.95 |

Three columns are presented under the "AcOH" heading, each of which relates to weight percentage of acetic acid. The "API" column identifies the amount of acetic acid in the lyophilizate (also termed the active principal ingredient), before hydration. The "Added" column identifies the amount of acetic acid, if any, added to the water used in the hydration process. A zero in the API column indicates that the optional acidification step was not employed. The Total column provides the total amount of acetic acid present in the composition, made up of the sum of the API and added columns. The Lanreotide column provides the weight percentage of lanreotide peptide in the finished composition. The pH column provides the pH value of the finished composition.

The examples 1-6 correspond to compositions prepared by a process according to the present invention and including a single lyophilization; the examples 7-9 correspond to compositions prepared by a process including two lyophilizations according to the process as described in the PCT application WO 99/48517.

CHARACTERISTICS OF THE COMPOSITIONS PREPARED IN EXAMPLES 1 To 9

Properties of the compositions prepared according to Examples 1 to 9 are tabulated in Table 2, below, and graphed in FIGS. 1 to 6.

TABLE 2

| Example | SIF | Flow Mean | Routine IVT Mean (% released) | | |
|---|---|---|---|---|---|
| No. | Mean (N) | (μl/min) | Q(2.75 h) | Q(9.25 h) | Q(24.25 h) |
| 1 | 18.9 | 96.8 | 18.7 | 53.3 | 92.5 |
| 2 | 21.4 | 83.0 | 17.5 | 51.2 | 91.6 |
| 3 | 21.8 | 83.5 | 17.3 | 48.8 | 89.4 |
| 4 | 30.3 | 9.9 | 15.8 | 46.0 | 87.1 |
| 5 | 25.4 | 34.0 | 18.4 | 52.1 | 92.0 |
| 6 | 17.2 | 144.8 | 19.5 | 54.7 | 94.7 |
| 7 | 24.4 | 56.1 | 17.0 | 48.2 | 88.3 |
| 8 | 17.3 | 136.9 | 20.7 | 57.6 | 95.2 |
| 9 | 26.7 | 1.0 | 15.7 | 45.5 | 84.5 |

Injectability of the compositions was measured both in terms of the strength required to discharge the syringe (syringe injection force or SIF) and the viscosity of the compositions, measured in terms of flow rate.

The flow rate method was developed based upon the principles of the reference NF EN ISO 1133: "Determination of the melt mass flow rate (MFR) and the melt volume flow rate (MVR) of thermoplastics". In this technique, the viscosity of the solution is determined indirectly, under temperature-controlled conditions, by measuring the flow throughout a standarised stainless-steel test syringe while a constant pressure is applied. The flow of the supersaturated gel through the syringe (which is proportional to the viscosity) is measured and expressed as a flow-rate (μl/min).

Syringe injection force (SIF) test was developed to assess the maximum force needed to discharge, at a constant displacement rate (200 mm/min), the formulation contained in the finished drug product syringe maintained in vertical position.

Release of the active ingredient was measured using an in vitro test (IVT), in which the percentage of the active component released (Q) was measured after 2.75 h, 9.25 h and 24.25 h. The in vitro released test was object of an specific development bearing in mind the special characteristics of the formulation for which none of the conventional in vitro dissolution apparatus was applicable. As a result, a small drug product holding device was developed to retain the formulation in a dialysis membrane. The in vitro dissolution profile is obtained in saline solution by using the pharmacopoeial dissolution (basket) apparatus, as described in the USP test <711> Dissolution, apparatus 1 and in the Eur. Pharm. 2.9.3 monograph.

Figure 1:
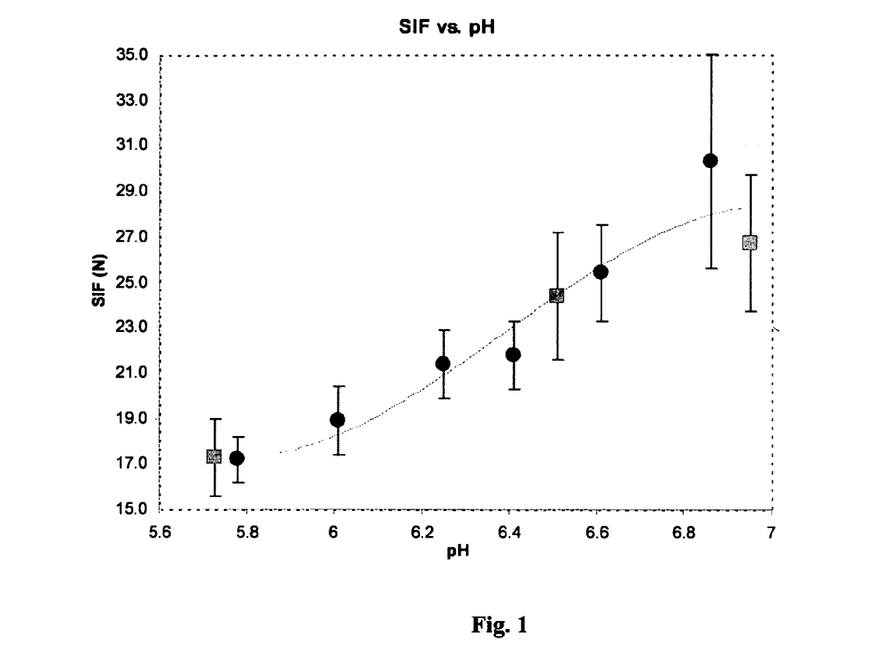
FIG. 1 is a plot of syringe injection force (SIF) (in Newtons) versus pH for compositions prepared by a process according to the invention including a single lyophilization (represented by filled circles) and compositions prepared by a process including two lyophilizations (represented by filled squares).

In FIG. 1, syringe injection force (SIF) is plotted against pH. The graph demonstrates that as the pH increases, the SIF also increases, and the extent of the SIF increase is not dependent on whether the single lyophilization process or double lyophilization process was employed.

Figure 2:
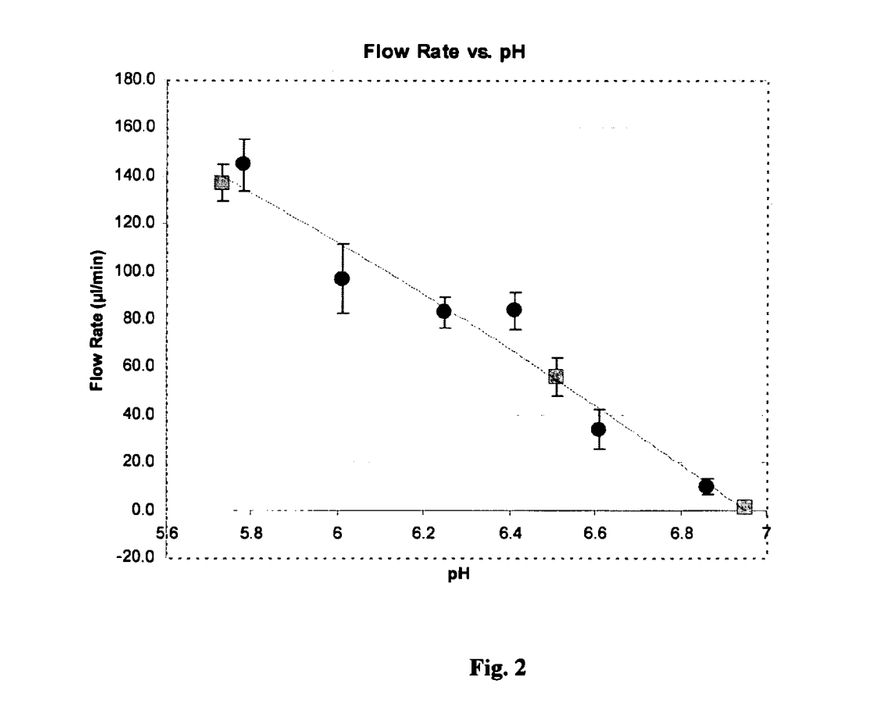
FIG. 2 is a plot of flow rate (micro-liters per minute) versus pH for compositions prepared by a process according to the invention including a single lyophilization (represented by filled circles) and compositions prepared by a process including two lyophilizations (represented by filled squares).

In FIG. 2, flow rate is plotted against pH. The flow rate is inversely proportional to pH in that as pH increases, the flow rate decreases. As with acetic acid concentration and SIF, the flow rate parameter is not influenced by whether the single lyophilization process or double lyophilization process was employed.

Figure 3:
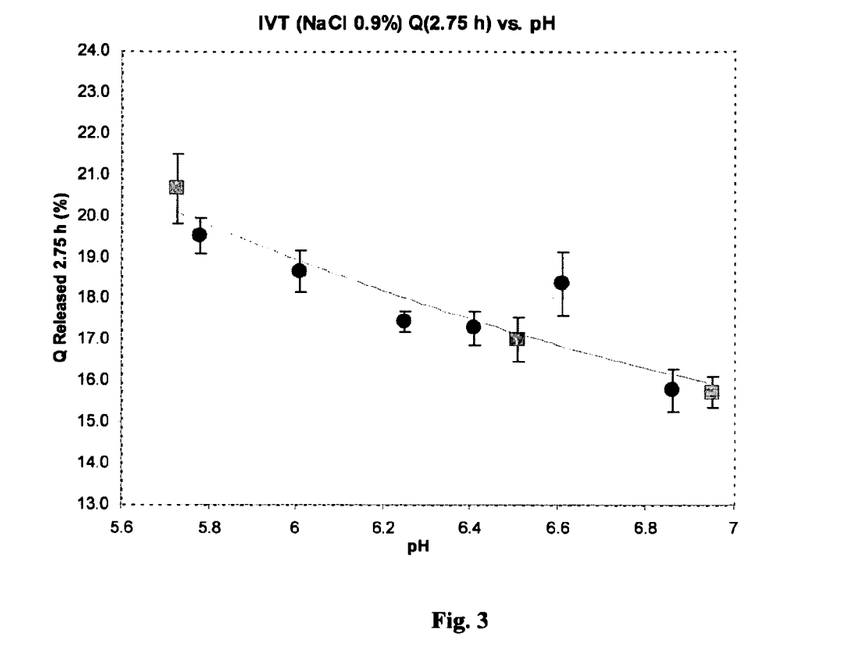
FIG. 3 is a plot showing the percentage of lanreotide acetate released after 2.75 hours versus pH during an in vitro test of compositions prepared by a process according to the invention including a single lyophilization (represented by filled circles) and compositions prepared by a process including two lyophilizations (represented by filled squares).
Figure 4:
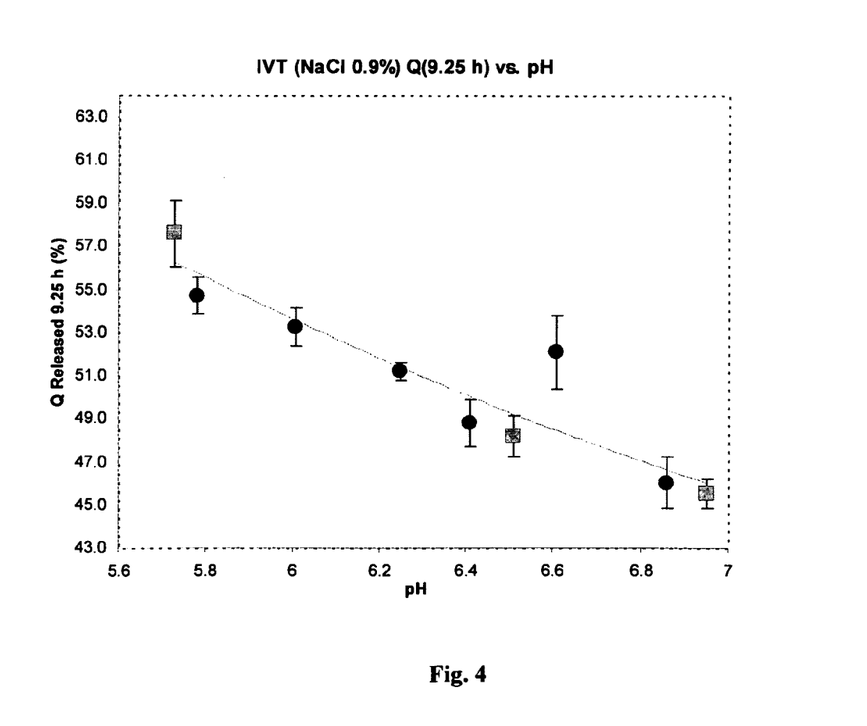
FIG. 4 is a plot showing the percentage of lanreotide acetate released after 9.25 hours versus pH during an in vitro test of compositions prepared by a process according to the invention including a single lyophilization (represented by filled circles) and compositions prepared by a process including two lyophilizations (represented by filled squares).
Figure 5:
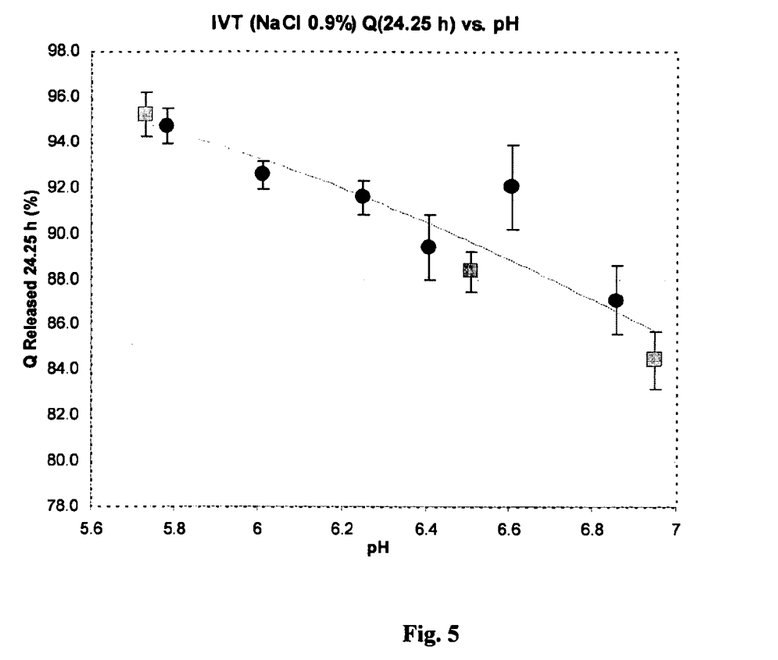
FIG. 5 is a plot showing the percentage of lanreotide acetate released after 24.25 hours versus pH during an in vitro test of compositions prepared by a process according to the invention including a single lyophilization (represented by filled circles) and compositions prepared by a process including two lyophilizations (represented by filled squares).
Figure 6:
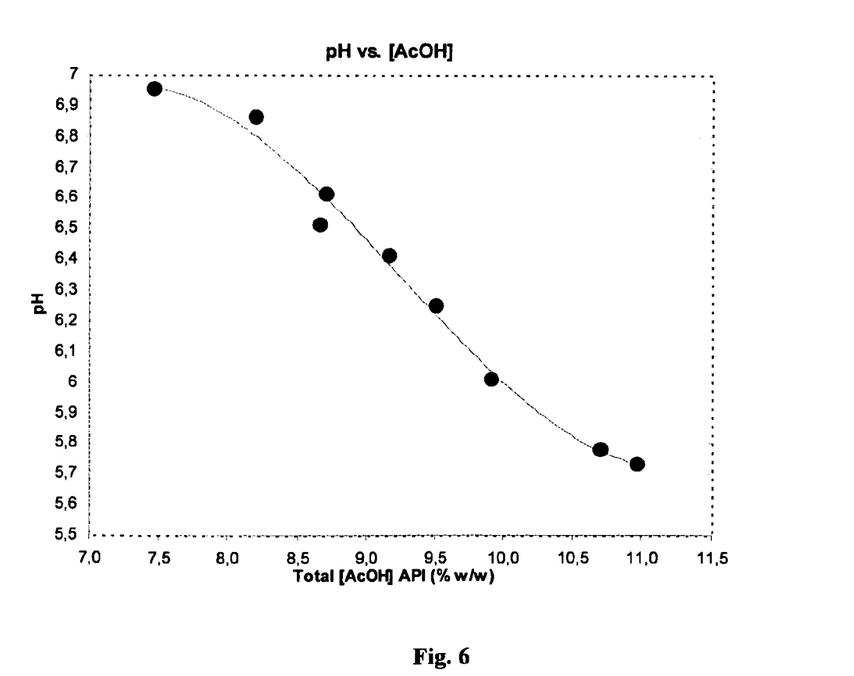
FIG. 6 is a plot showing the relation between the acetate content (AcOH level) and the pH of the composition. Data of pH are plotted in function of the acetate content in % (w/w) of the active substance.

In FIGS. 3, 4 and 5, the proportion of the active ingredient released is plotted against pH during an in vitro test of the compositions, measured after 2.75 hours, 9.25 hours and 24.25 hours, respectively. The graphs demonstrate that the release rate decreases with increasing pH when the concentration is kept constant.

EXAMPLE 10

Preferred Procedure for the Preparation of Compositions According to the Invention A pre-lyophilization pool was prepared by dissolving 25 g/l pure lanreotide [BIM-23014] in an aqueous solution of 15% acetic acid solution. The pool was loaded into a hollow metal tray and cooled from room temperature to 2° C. over 10 minutes and then held at this temperature for 3 hours. The cooled mixture was then frozen to −40° C. over 10 minutes and then held at this temperature for 2.75 hours. A vacuum to 20 μbar was applied and maintained while the mixture was heated from −40° C. to 25° C. over 20 hours and further heated to 35° C. for 16.75 hours.

Water for injection was acidified with glacial acetic acid sufficient to provide a final anhydrous acetate content of 9.6% to 10%. The acidified water and lanreotide acetate were then combined to a concentration of 24.6% pure lanreotide and 9.6% to 10% anhydrous acetate as follows: the lanreotide acetate and water were weighed and placed into two separate cylinders, fitted with pistons and linked together via a three-way valve. Prior to hydration, a vacuum of between 100 and 600 μbar was applied to the cylinder containing the lanreotide acetate powder via the three-way valve. The water was then introduced into the cylinder containing the lanreotide acetate, again via the three-way valve. The lanreotide acetate then underwent static hydration for at least two hours. The dispersion was then homogenised by passing the contents back and forth between the two cylinders, using the pistons. The process yielded a lanreotide acetate supersaturated gel of pH 6.2.

While the present invention has been described with reference to one specific embodiment, it will be appreciated that various modifications and changes could be made without departing from the scope of the invention.

The invention claimed is:

1. A method for preparing an injectable sustained release pharmaceutical composition, comprising the steps of:

lyophilizing a mixture of a lanreotide salt and an aqueous acid solution in a stepwise temperature pattern, wherein the stepwise temperature pattern is:
  initially reduced from room temperature to 2° C.±1° C. and then held constant;
  further reduced from 2±1° C. to −40±5° C. and then held constant;
  increased from −40±5° C. to 25±5° C. and then held constant; and
  further increased to 35±5° C. and then held constant; the resulting mixture to form a lyophilizate; and
hydrating the lyophilizate; wherein the composition has a final pH ranging between pH 5.8 to 6.4; and the method comprising only one lyophilization.

2. The method of claim 1, wherein the acid is acetic acid.

3. The method of claim 1, wherein the aqueous acid solution comprises acetic acid in a concentration sufficient to provide a pH that ranges between 5 to 7.

4. The method of claim 1, wherein the aqueous acid solution used to hydrate the lyophilizate comprises a concentration of acetic acid to provide an anhydrous acetate content of 9.1 to 10.5% by weight.

5. The method of claim 1, wherein the mixture of a lanreotide salt and an aqueous acid solution comprises 25 ±2 g/l of the lanreotide salt and 15±2% by weight acetic acid.

6. The method of claim 1 wherein the lyophilizing is for a duration of at least 40 hours.

7. The method of claim 1 wherein the mixture, during the lyophilization step, has a temporal pattern that is:
  initially reduced up to 30 minutes and then held constant for 3±1 hours;
  further reduced up to 15 minutes and then held constant for 3.5±1 hours;
  increased over 20±5 hours and then held constant for at least 40 hours; and
  further increased over 1±0.5 hours and then held constant for at least 16 hours.

8. The method of claim 1 wherein the mixture, after the temperature is reduced, has an atmospheric pressure that is reduced to 20±5 μbar and said atmospheric pressure remains constant as the temperature of the mixture increases.

9. The method of claim 1, wherein the lyophilizate is dissolved in an amount of water that is less than 50% of the amount needed to completely dissolve the somatostatin analog salt and adapted to give the composition a semi-solid consistency.

10. A sustained release pharmaceutical composition prepared according to the process of claim 1.

11. The composition of claim 10, wherein the composition comprises lanreotide that is capable of in vivo release over a period of at least 15 days.

12. The composition of claim 11 comprising between 15% and 35% by weight lanreotide base.

13. The composition of claim 10 suitable for use after storage at between 2 and 8° C. for more than 12 months.

14. The method of claim 1, wherein the lyophilization step is for a duration of at least 60 hours.

15. The method of claim 7, wherein the mixture, during the lyophilization step, has a temperature that is:
  initially reduced up to 10 minutes and then held constant for 3±1 hours;
  further reduced up to 10 minutes and then held constant for 3.5±1 hours;
  increased over 20±5 hours and then held constant for at least 40 hours; and
  further increased over 1±0.5 hours and then held constant for at least 16 hours.

16. The process method of claim 9, wherein the amount of water is less than 30%.

17. The method of claim 9, wherein the amount of water is less than 10%.

18. The composition of claim 9, wherein the in vivo release is over a period of 1 month.

19. The composition of claim 11, wherein the in vivo release is over a period of 2 months.

20. The composition of claim 12, comprising between 15% and 25±5% by weight lanreotide base.

21. The composition of claim 12, comprising between 15% and approximately 24.6±2.5% by weight lanreotide base.

22. The composition of claim 10 suitable for use after storage at between 2 and 8° C. for more than 24 months.

* * * * *